United States Patent
Mastri et al.

(10) Patent No.: US 10,159,809 B2
(45) Date of Patent: Dec. 25, 2018

(54) MULTIPATH FILTER ASSEMBLY WITH INTEGRATED GASEOUS SEAL FOR MULTIMODAL SURGICAL GAS DELIVERY SYSTEM

(71) Applicant: Surgiquest, Inc., Milford, CT (US)

(72) Inventors: Dominick Mastri, Bridgeport, CT (US); Earl M. Zergiebel, Guilford, CT (US); Michael J. Augelli, Prospect, CT (US); Kenneth Blier, Cheshire, CT (US); Ralph Stearns, Bozrah, CT (US)

(73) Assignee: Surgiquest, Inc., Milford, CT (US)

( * ) Notice: Subject to any disclaimer, the term of this patent is extended or adjusted under 35 U.S.C. 154(b) by 199 days.

(21) Appl. No.: 15/177,532

(22) Filed: Jun. 9, 2016

(65) Prior Publication Data

US 2016/0287817 A1    Oct. 6, 2016

Related U.S. Application Data

(63) Continuation-in-part of application No. 14/628,711, filed on Feb. 23, 2015, now Pat. No. 9,387,296, and
(Continued)

(51) Int. Cl.
*A61M 13/00* (2006.01)
*A61M 39/02* (2006.01)
(Continued)

(52) U.S. Cl.
CPC ....... *A61M 13/006* (2014.02); *A61B 17/3474* (2013.01); *A61M 5/165* (2013.01);
(Continued)

(58) Field of Classification Search
CPC .............. A61M 13/006; A61M 13/003; A61M 2205/075; A61M 2210/1021;
(Continued)

(56) References Cited

U.S. PATENT DOCUMENTS 7,854,724 B2   12/2010  Stearns et al.
7,976,598 B2    7/2011  Matula et al.
(Continued)

FOREIGN PATENT DOCUMENTS

EP        2226027 A1      9/2010
WO    WO-2008077080 A2    6/2008
(Continued)

OTHER PUBLICATIONS

International Search Report dated Aug. 26, 2016 in connection with PCT/US2016/037976.
(Continued)

*Primary Examiner* — Jenna Zhang
(74) *Attorney, Agent, or Firm* — Locke Lord LLP; Scott D. Wofsy

(57) ABSTRACT

A gas conditioning unit for a surgical gas delivery device is disclosed, which includes a filter housing having an insufflation gas flow path for delivering insufflation gas to a body cavity and for facilitating pressure measurements from the body cavity, a pressurized gas flow path for delivering pressurized gas from a pump in the surgical gas delivery device to an internal nozzle in the filter housing that accelerates the pressurized gas and thereby generates a continuous pressure barrier that inhibits egress of insufflation gas from the body cavity, a vacuum return flow path for returning depressurized gas spent by the internal nozzle back to the pump under vacuum, an air entrainment flow path for drawing air into the body cavity to maintain a given pressure therein, and a smoke evacuation flow path for conveying smoke from the body cavity.

32 Claims, 11 Drawing Sheets

Related U.S. Application Data a continuation-in-part of application No. 14/609,952, filed on Jan. 30, 2015, now Pat. No. 9,387,295.

(60) Provisional application No. 62/186,549, filed on Jun. 30, 2015.

(51) Int. Cl.
| | | |
|---|---|---|
| *A61B 17/34* | (2006.01) | |
| *A61M 5/165* | (2006.01) | |
| *B01D 46/00* | (2006.01) | |
| *B01D 51/10* | (2006.01) | |

(52) U.S. Cl.
CPC .......... *A61M 13/003* (2013.01); *A61M 39/02* (2013.01); *A61B 2218/008* (2013.01); *A61M 2202/0225* (2013.01); *A61M 2205/12* (2013.01); *A61M 2205/3344* (2013.01); *A61M 2205/75* (2013.01); *A61M 2210/1021* (2013.01); *B01D 46/0008* (2013.01); *B01D 46/0019* (2013.01); *B01D 51/10* (2013.01)

(58) Field of Classification Search
CPC ................ A61M 13/165; A61M 39/02; A61M 2205/3344; A61M 2205/12; A61M 2205/75; A61M 2202/0225; A61B 2218/006; A61B 2218/008; A61B 17/3474; B01D 46/0008; B01D 46/0019; B01D 51/10

See application file for complete search history.

(56) References Cited

U.S. PATENT DOCUMENTS

| | | | | |
|---|---|---|---|---|
| 7,981,072 | B2* | 7/2011 | Uesugi | A61M 13/003 600/560 |
| 8,088,189 | B2 | 1/2012 | Matula et al. | |
| 8,795,223 | B2 | 8/2014 | Stearns et al. | |
| 9,067,030 | B2 | 6/2015 | Stearns et al. | |
| 2002/0128603 | A1* | 9/2002 | Booth | A61B 17/3421 604/164.01 |
| 2004/0102731 | A1* | 5/2004 | Blackhurst | A61B 1/00154 604/26 |
| 2005/0015043 | A1* | 1/2005 | Stubbs | A61B 17/3421 604/26 |
| 2007/0088275 | A1* | 4/2007 | Stearns | A61M 1/28 604/164.01 |
| 2007/0163585 | A1* | 7/2007 | Uesugi | A61M 13/003 128/204.18 |
| 2010/0170208 | A1* | 7/2010 | Matula | A61M 13/003 55/344 |
| 2010/0185139 | A1 | 7/2010 | Stearns et al. | |
| 2010/0280437 | A1 | 11/2010 | Muir | |
| 2012/0138523 | A1 | 6/2012 | Matula et al. | |
| 2012/0150101 | A1* | 6/2012 | Stearns | A61B 17/3421 604/24 |
| 2012/0245511 | A1* | 9/2012 | Stearns | A61B 17/3462 604/26 |
| 2013/0231606 | A1 | 9/2013 | Stearns et al. | |
| 2014/0074015 | A1* | 3/2014 | Mastri | A61M 13/003 604/26 |
| 2014/0171855 | A1 | 6/2014 | Mastri et al. | |

FOREIGN PATENT DOCUMENTS

| | | |
|---|---|---|
| WO | WO-20100042204 A2 | 4/2010 |
| WO | WO-2013142150 A1 | 9/2013 |
| WO | WO-2016123173 A1 | 8/2016 |

OTHER PUBLICATIONS

Written Opinion dated Aug. 26, 2016 in connection with PCT/US2016/037976.

International Search Report dated May 3, 2016 in connection with PCT/US2016/015042.

Written Opinion dated May 3, 2016 in connection with PCT/US2016/015042.

\* cited by examiner

MULTIPATH FILTER ASSEMBLY WITH INTEGRATED GASEOUS SEAL FOR MULTIMODAL SURGICAL GAS DELIVERY SYSTEM

CROSS-REFERENCE TO RELATED APPLICATIONS

The subject application claims the benefit of priority from U.S. Provisional Patent Application Ser. No. 62/186,549 filed Jun. 30, 2015, and is a continuation-in-part of co-pending U.S. patent application Ser. No. 14/628,711 filed Feb. 23, 2015, which is a continuation-in-part of co-pending U.S. application Ser. No. 14/609,952 filed Jan. 30, 2015, each of which is incorporated herein by reference in its entirety.

BACKGROUND OF THE INVENTION

1. Field of the Invention

The subject invention is directed to surgery, and more particularly, to a filter device for a multimodal gas delivery system used during surgical procedures, such as, for example, laparoscopic surgical procedures performed in the abdominal cavity of a patient, single incision laparoscopic surgery or transluminal surgical procedures performed through a body lumen of the patient, such as, for example, trans-anal minimally invasive surgery.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

SurgiQuest, Inc., Milford, Conn. USA has developed unique surgical access devices that permit ready access to an insufflated surgical cavity without the need for conventional mechanical seals, and it has developed related gas delivery systems for providing sufficient pressure and flow rates to such access devices, as described in whole or in part in U.S. Pat. Nos. 7,854,724 and 8,795,223, the disclosures of which are both herein incorporated by reference in their entireties.

The present invention relates to a multimodal gas delivery system and related devices for performing multiple surgical gas delivery functions, including insufflation, recirculation and filtration of insufflation fluids and gases during surgical procedures including laparoscopic surgery, single incision laparoscopic surgery and transluminal minimally invasive surgery. The use of a single multimodal system reduces operating costs by requiring the purchase of only one system while achieving multiple functions, and also thereby reduces the amount of equipment needed in an operating room, thus reducing clutter and allowing space for other necessary equipment.

SUMMARY OF THE INVENTION

The subject invention is directed to a new and useful system for delivering gas during a surgical procedure, such as, for example, during laparoscopic procedures performed in the abdominal cavity of a patient or transluminal procedures performed through a body lumen of a patient, such as trans-anal minimally invasive surgery.

The system includes a gas delivery device having a main housing including a port for receiving insufflation gas from a gas source and enclosing a pump assembly for circulating gas throughout the system, and a gas conditioning unit configured for operative association with the gas delivery device.

The gas conditioning unit includes an insufflation gas flow path for delivering insufflation gas to the body cavity or lumen and for facilitating periodic static pressure measurements from the body cavity or lumen. The gas conditioning unit further includes a pressurized gas flow path for delivering pressurized gas from the pump to an internal nozzle assembly configured to accelerate the pressurized gas and thereby generate a continuous pressure barrier contained within the gas conditioning unit that inhibits egress of insufflation gas from the body cavity or lumen.

The gas conditioning unit also includes a vacuum return flow path for returning depressurized gas spent by the internal nozzle assembly back to the pump under vacuum, an air entrainment flow path for drawing air into the body cavity or lumen to maintain a given pressure therein under certain abnormal operating conditions, and a smoke evacuation flow path for conveying smoke and debris from the body cavity or lumen.

Preferably, the gas conditioning unit includes a generally cylindrical filter housing having a front end and an opposed rear end, and the gas delivery unit includes an engagement port for detachably receiving the rear end of the gas conditioning unit. Each flow path defined within the filter housing has a filter element associated therewith for conditioning or otherwise filtering gas flowing therethrough.

The air entrainment flow path and the smoke evacuation flow path share a common filter element in the form of a pleated filter element. The vacuum return flow path and the pressurized gas flow path each have a separate pleated filter element associated therewith. The insufflation gas flow path has a non-woven membrane filter element associated therewith.

The rear end of the filter housing includes a first inlet port communicating with the insufflation gas flow path, a second inlet port communicating with the pressurized gas flow path, and a first outlet port communicating with the vacuum return path. The front end of the filter housing includes a second outlet port communicating with the insufflation gas flow path, a primary central port communicating with the smoke evacuation flow path and the air entrainment flow path, and a plurality of spaced apart vent ports communicating with the smoke evacuation flow path and the air entrainment flow path.

The first inlet port in the rear end of the filter housing communicates with the source of insufflation gas. The second inlet port in the rear end of the filter housing communicates with an outlet of the pump. The first outlet port in the rear end of the filter housing communicates with an inlet of the pump.

When the system is employed to delivery gas during laparoscopic surgery, for example, a first surgical access device or trocar is in fluid communication with second outlet port of the filter housing through a first flexible tube, and a second surgical access device or trocar is in fluid communication with the primary central port of the filter housing through a second flexible tube. When the system is employed to deliver gas during trans-anal minimally invasive surgery or single incision laparoscopic surgery, for example, a multiport access device is operatively associated with the primary central port and the second outlet port of the filter housing to provide simultaneous access for multiple surgical devices or tools through a single incision or natural body orifice.

Preferably, the spaced apart vent ports in the front end of the filter housing are open to atmosphere. The filter housing preferably includes an internal pressure chamber within the pressurized gas flow path located upstream from the internal nozzle assembly, and an internal reservoir chamber located within the vacuum return flow path upstream from the pump.

The subject invention is also directed to an access device for use when the system is employed to deliver gas during trans-anal minimally invasive surgery or single incision laparoscopic surgery. The access device includes an elongated tubular body portion adapted and configured for introduction through a natural orifice of a body lumen or through a single incision formed in the abdominal wall of a patient. A first connective fitting is preferably associated with a proximal end portion of the tubular body portion for connecting with a first conduit that facilitates the delivery of insufflation gas to the body lumen or abdominal cavity of the patient.

A multiport end cap is operatively associated with the proximal end portion of the tubular body portion and it includes a plurality of separate access ports for accommodating the introduction of individual surgical instruments into the body lumen or abdominal cavity of the patient. A second connective fitting is preferably associated with the multiport end cap for connecting with a second conduit that facilitates smoke evacuation from and air entrainment into the body lumen or abdominal cavity of a patient. In another embodiment, the second connective fitting can be associated with the proximal end portion of the tubular body portion, rather than the end cap.

Preferably, the tubular body portion includes a distal annular flange for securing the tubular body portion against the inner surface of the abdominal wall of the patient. An adjustable engagement ring is operatively associated with the proximal end portion of the tubular body portion for receiving and removably retaining a multiport end cap. The first connective fitting is associated with the engagement ring and it communicates with a conduit tube that extends into the tubular body portion and the conduit tube can extend along an interior wall of the tubular body portion toward the distal end of the tubular body portion. In another embodiment, the second connective fitting can be associated with the engagement ring.

The multiport end cap preferably includes three separate access ports, although it can have more than three or less than three depending upon the application or surgical procedure for which it is employed. In an embodiment of the subject invention, the three separate access ports have the same or a common diameter. In another embodiment of the subject invention, the one of the three separate access ports have a different diameter than the other two access ports, which may be greater or less than that of the others.

These and other features of the surgical gas delivery system and the gas conditioning device of the subject invention and the manner in which both are manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the multipath filter assembly of the subject invention without undue experimentation, preferred embodiments thereof will be described in detail herein below with reference to certain figures, wherein.

DETAILED DESCRIPTION OF PREFERRED EMBODIMENTS

Figure 1:
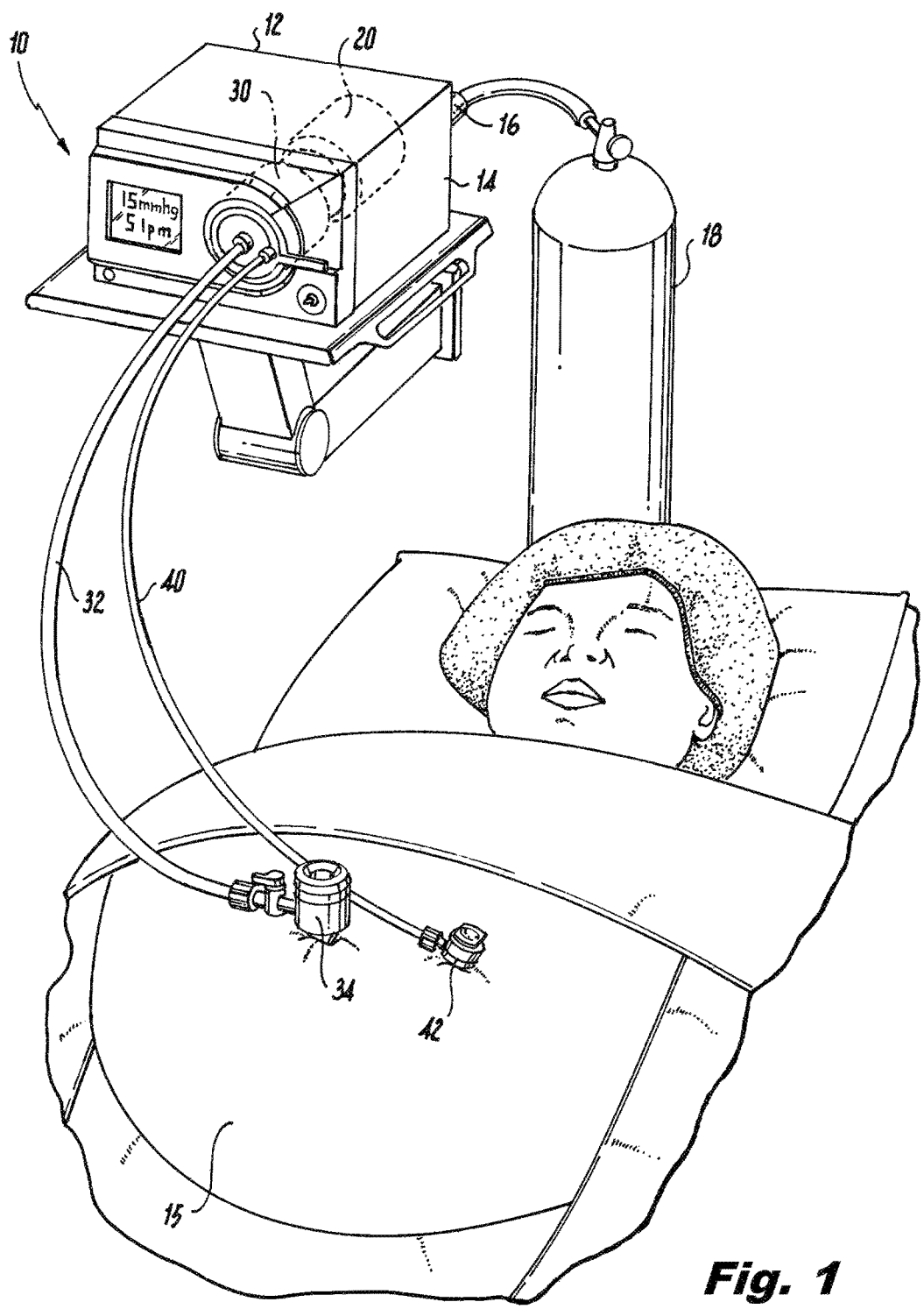
FIG. 1 is an illustration of the operating environment in which the gas delivery system of the subject invention is employed during a laparoscopic surgical procedure, which includes, among other things, a gas delivery device having a housing with a port for receiving pressurized insufflation gas from a gas source, and a separate gas conditioning unit configured for operative association with the gas delivery device.
Figure 2:
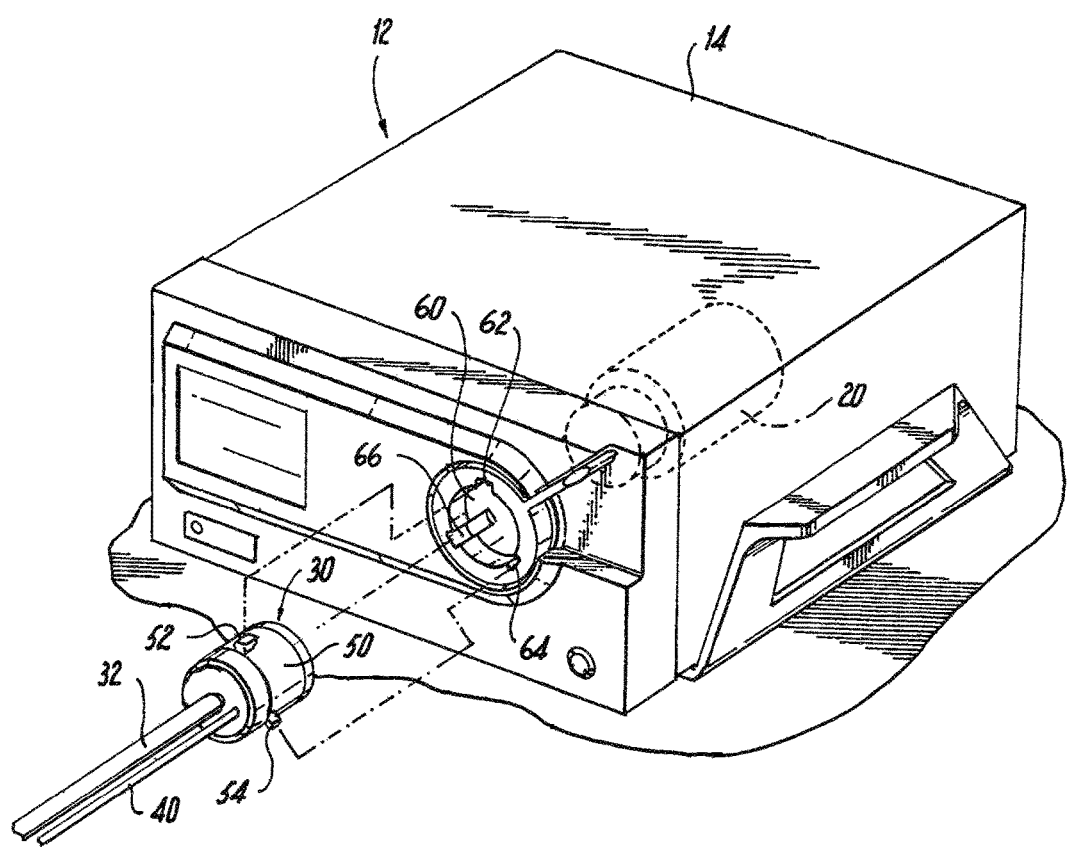
FIG. 2 is a perspective view of the gas delivery device and the separate gas conditioning unit illustrated in FIG. 1, at a time when the gas conditioning unit is not installed in the gas delivery device.

Referring now to the drawings wherein like reference numerals identify similar structural features or aspects of the subject invention, there is illustrated in FIGS. 1 and 2, a new and useful system for delivering and circulating medical gas (e.g., carbon dioxide) during a minimally invasive surgical procedure, such as a laparoscopic surgical procedure performed within a patient's abdominal cavity. Alternative uses may involve endoscopic surgical procedures performed through a natural orifice or lumen.

The gas delivery system, which is designated generally by reference numeral 10, includes, among other things, a gas delivery device 12 having a housing 14 with a rear connector or port 16 for receiving pressurized insufflation gas from a gas source 18. As shown, the gas source 18 is a portable supply canister. However, it is envisioned that the medical or insufflating gas could be supplied from another source, including for example, a remote storage tank (e.g., house gas) as is well known in the art. A compressor or pump assembly 20 is enclosed within the housing 14 of gas delivery device 12 for circulating pressurized gas throughout the system 10 to maintain a stable abdominal cavity pressure or pneumo-peritoneum during a laparoscopic surgical procedure.

A graphical user interface 25 having associated control circuitry is provided within the housing 14 of gas delivery device 12 for controlling the operation of the pump assembly 20, as well as the delivery of insufflating gas from supply source 18. The interface and associated circuitry enables a user to readily adjust flow rates and supply pressures relating to the delivery, circulation and recirculation of gas and fluid throughout the system.

The gas delivery system 10 further includes a separate and preferably disposable gas conditioning unit 30, which is dimensioned and configured for operative association with the gas delivery device 12. As described in more detail below, the gas conditioning unit 30 of the subject invention is constructed in such a manner so that a continuous gaseous pressure barrier is generated within the interior of the housing of the gas conditioning unit itself, remote from the patient. During a laparoscopic surgical procedure, this gaseous pressure barrier or working zone prevents the egress of insufflation gas from the abdominal cavity of the patient 15, while maintaining a stable pneumoperitoneum within the abdominal cavity. Similarly, during a transluminal procedure, such as, for example, trans-anal minimally invasive surgery (TAMIS), the gaseous pressure barrier prevents the egress of insufflation gas from the intestinal tract of the patient.

This feature differs from the multi-modal gas delivery systems disclosed in commonly assigned U.S. Pat. Nos. 7,854,724 and 8,795,223, wherein the gaseous pressure barrier is generated within the housing of a specialized trocar directly located at the surgical site, and the filtration of gases flowing through the system is accomplished using a disposable gas conditioning unit of the type that is disclosed in commonly assigned U.S. Pat. No. 9,067,030, which is incorporated herein by reference in its entirety.

The gas conditioning unit 30 of the subject invention will be described in detail below. Initially however, a brief description of the internal gas flow paths that are defined within the housing of the gas conditioning unit 30 will be described. More particularly, the gas conditioning unit 30 includes a number of internal gas flow paths configured to facilitate the periodic delivery of insufflating gas, as well as the continuous circulation and recirculation of pressurized gas.

Figure 6:
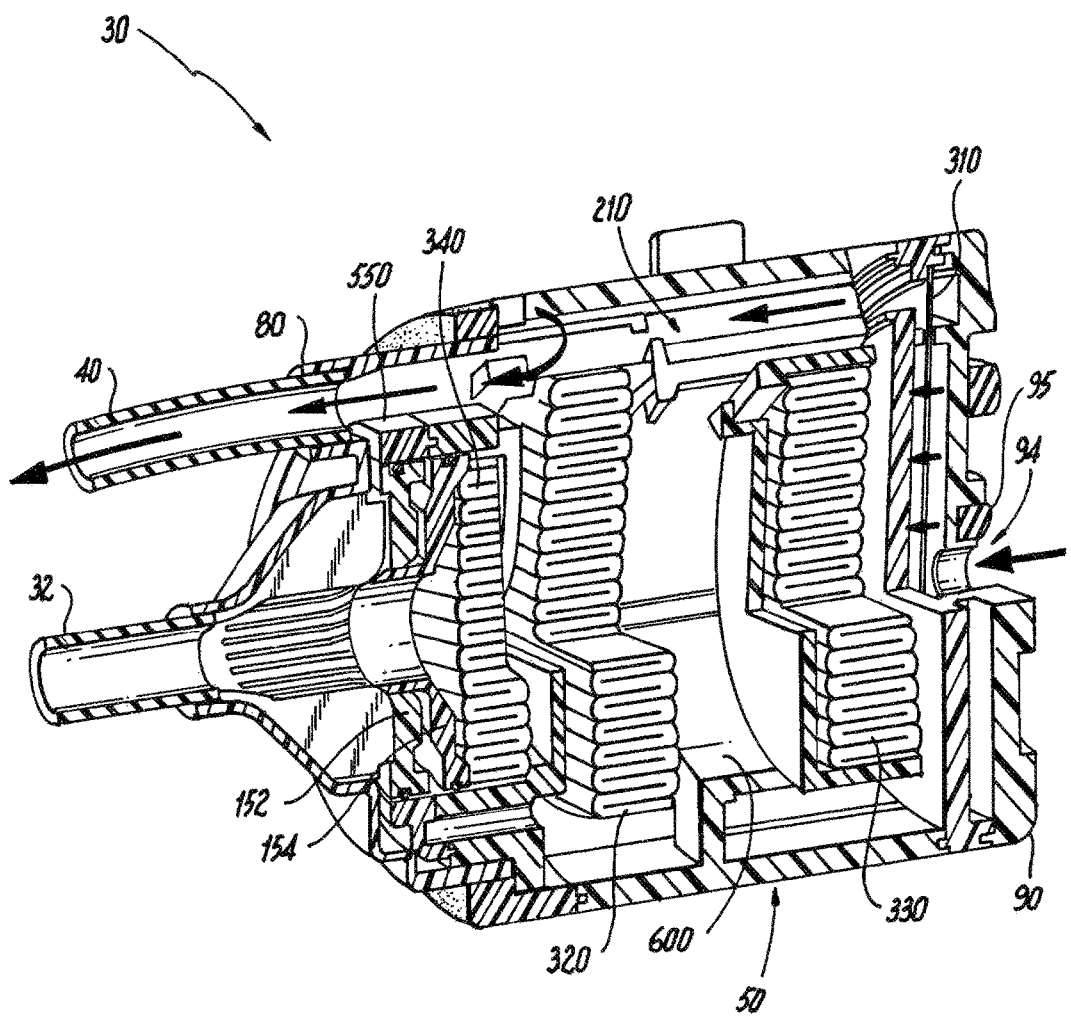
FIG. 6 is a cross-sectional view of the gas conditioning unit similar to the view shown in FIG. 5, with directional arrows illustrating the insufflation gas flow path (and sensing flow path) extending from an inlet port in the rear end of the filter housing to an outlet port in the front end of the filter housing.
Figure 11:
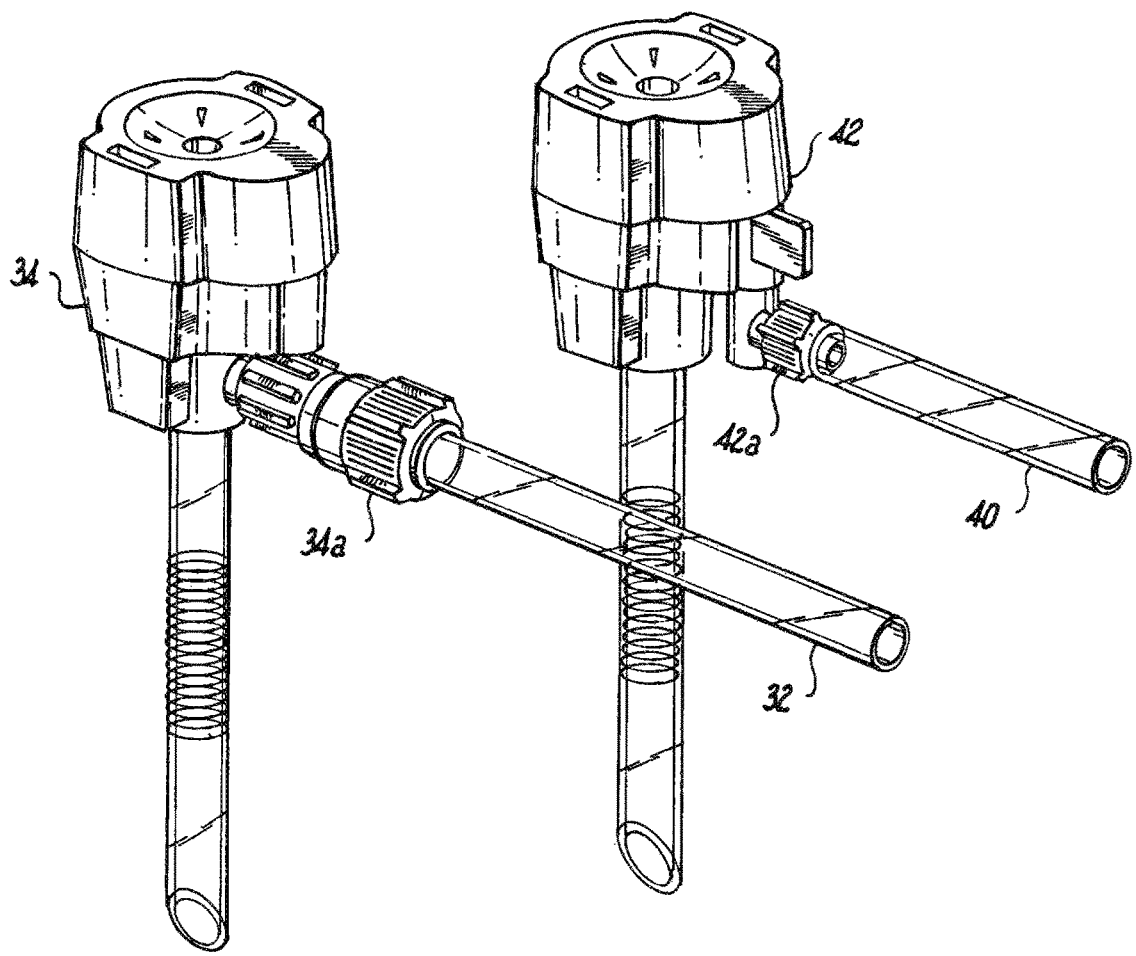
FIG. 11 is a perspective view of an arrangement of two surgical access device or trocars for operative association with the gas conditioning unit of FIG. 3 during a laparoscopic surgical procedure as seen in FIG. 1, wherein one access device is connected to the insufflation gas flow path and the other is connected to the smoke evacuation and gas entrainment flow paths.

In particular, the gas conditioning unit 30 includes a sense/insufflation flow path 210 indicated by the directional arrows shown in FIG. 6, which is configured to deliver insufflating gas from the gas delivery device 12 to the abdominal cavity of the patient 15 by way of a conduit 40 connected to a surgical access device or cannula 42, as seen in FIGS. 1 and 11. In addition, flow path 210 is configured to facilitate periodic static pressure measurements from the abdominal cavity through cannula 42. The duration of the insufflation interval between pressure measurements can vary, depending upon the patient and the operating environment. Typically, the flow and stop intervals are measured in milliseconds. This flow and stop methodology for obtaining static pressure measurements from the abdominal cavity is well known in the art.

Figure 7:
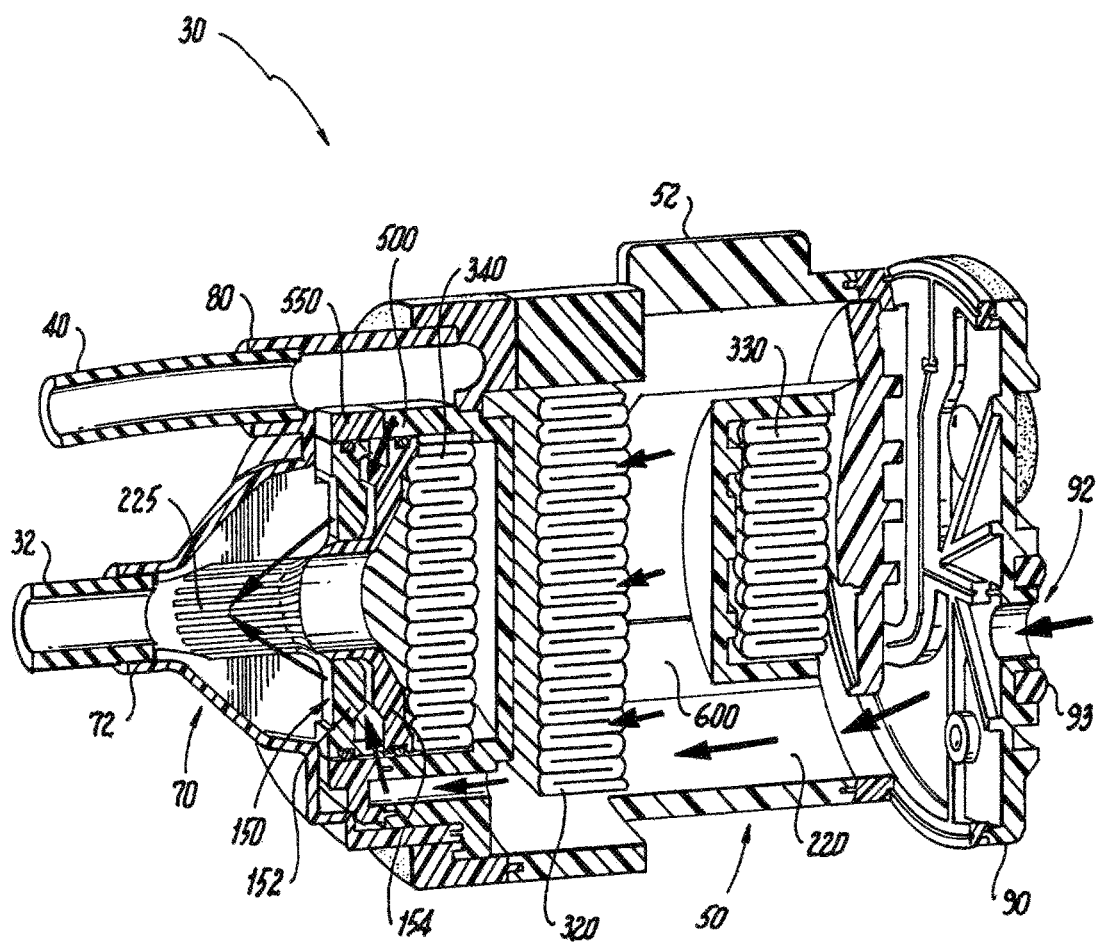
FIG. 7 is a cross-sectional view of the gas conditioning unit similar to the view shown in FIG. 5, with directional arrows illustrating the pressurized gas flow path extending from an inlet port in the rear end of the filter housing to a primary central port in the front end of the filter housing.

Gas conditioning unit 30 further includes a pressurized gas flow path 220 indicated by the directional arrows shown in FIG. 7, which is configured to receive pressurized gas from the pump assembly or compressor 20 of the gas delivery device 12. The pressurized gas flow path 220 is associated with a main conduit 32 that is connected to a surgical access device or trocar 34, as seen in FIGS. 1 and 11. The trocar 34 is the primary path for introducing surgical instrumentation into the abdominal cavity 15 of a patient during a laparoscopic surgical procedure, and it has a mechanical seal installed therein. The pressurized gas is used to create a pressure barrier within the throat region 225 at the front end cap 70 of the housing 50 of the gas conditioning unit 30. The pressure barrier prevents the egress of gas from the abdominal cavity 15 by way of conduit 32. In doing so, it also maintains a stable pneumoperitoneum within the abdominal cavity of the patient 15. The pressure barrier is generated by delivering pressurized gas to a nozzle assembly 150 located within the housing 50. The nozzle assembly 150 includes upper and lower jet rings 152 and 154 that use the pressurized gas to produce a high velocity gas flow that forms the pressure barrier in the throat region 225.

The construction of the nozzle assembly 150 is disclosed in more detail in commonly assigned U.S. Pat. No. 8,795,223, which is incorporated herein by reference in its entirety. As explained therein, the throat region 225 incudes air management features that control the inward and outward flows of gas, which contribute to the efficiency of the device to create the air barrier. The bowl-like throat area is shaped to allow pressurized gas coming out of the jet rings 152 and 154 to form a gaseous pressure barrier. There is a set of circumferentially spaced apart elongated fins within the throat region 225 that allow the expanded or spent pressurized gas to return to the compressor without colliding with the incoming gas. This management of the inward and outward flows of gas contributes to the efficiency of the device to create the air barrier.

Figure 8:
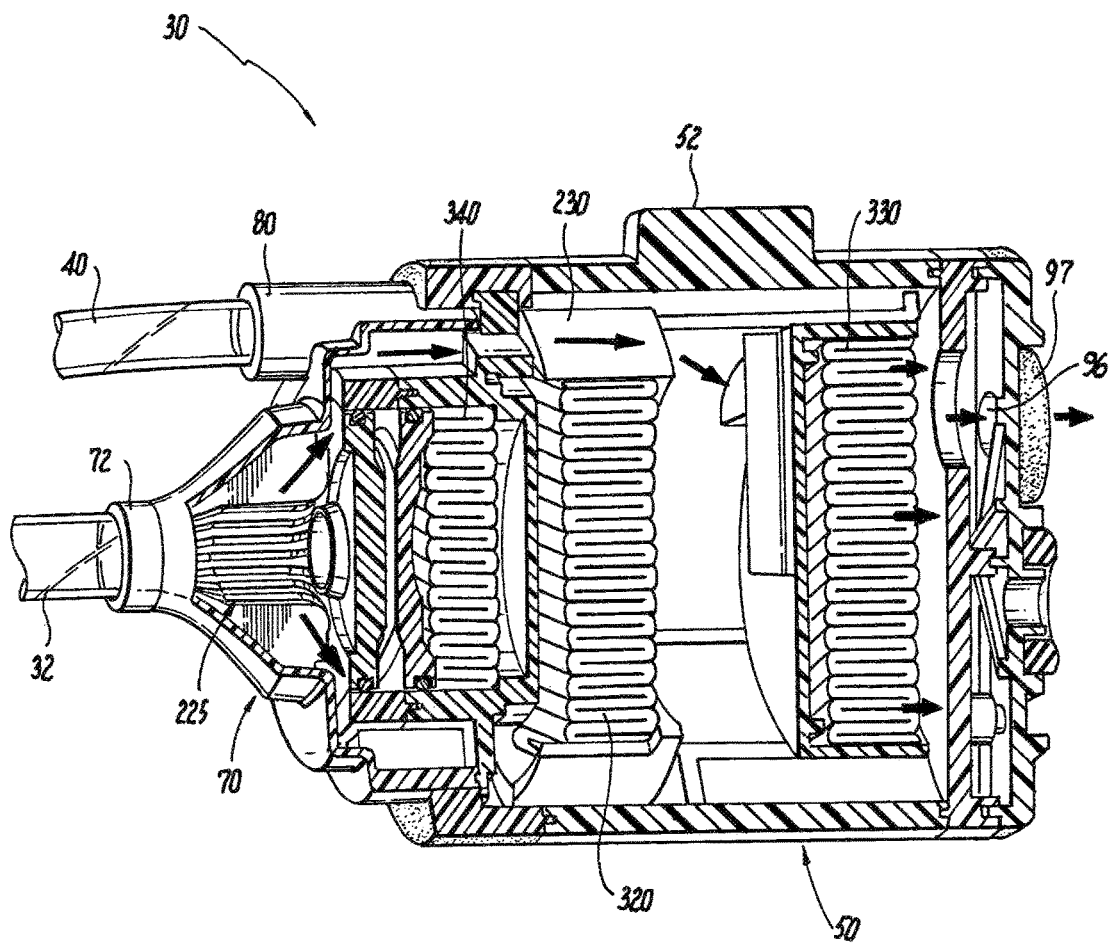
FIG. 8 is a cross-sectional view of the gas conditioning unit similar to the view shown in FIG. 5, with directional arrows illustrating the vacuum return flow path extending from the primary central port in the front end of the filter housing to an outlet port in the rear end of the filter housing.

The gas conditioning unit 30 also includes a vacuum return path 230 indicated by the directional arrows shown in FIG. 8, which is configured to return the spent pressurized gas to the pump assembly 20 of the gas delivery device 12. The gas returned to the pump assembly 20 is the spent pressurized gas that was used to create the pressure barrier within the throat region 225 of the gas conditioning unit 30. Moreover, it is the expanded gas that is efficiently managed by the fins within the throat region 225.

Figure 9:
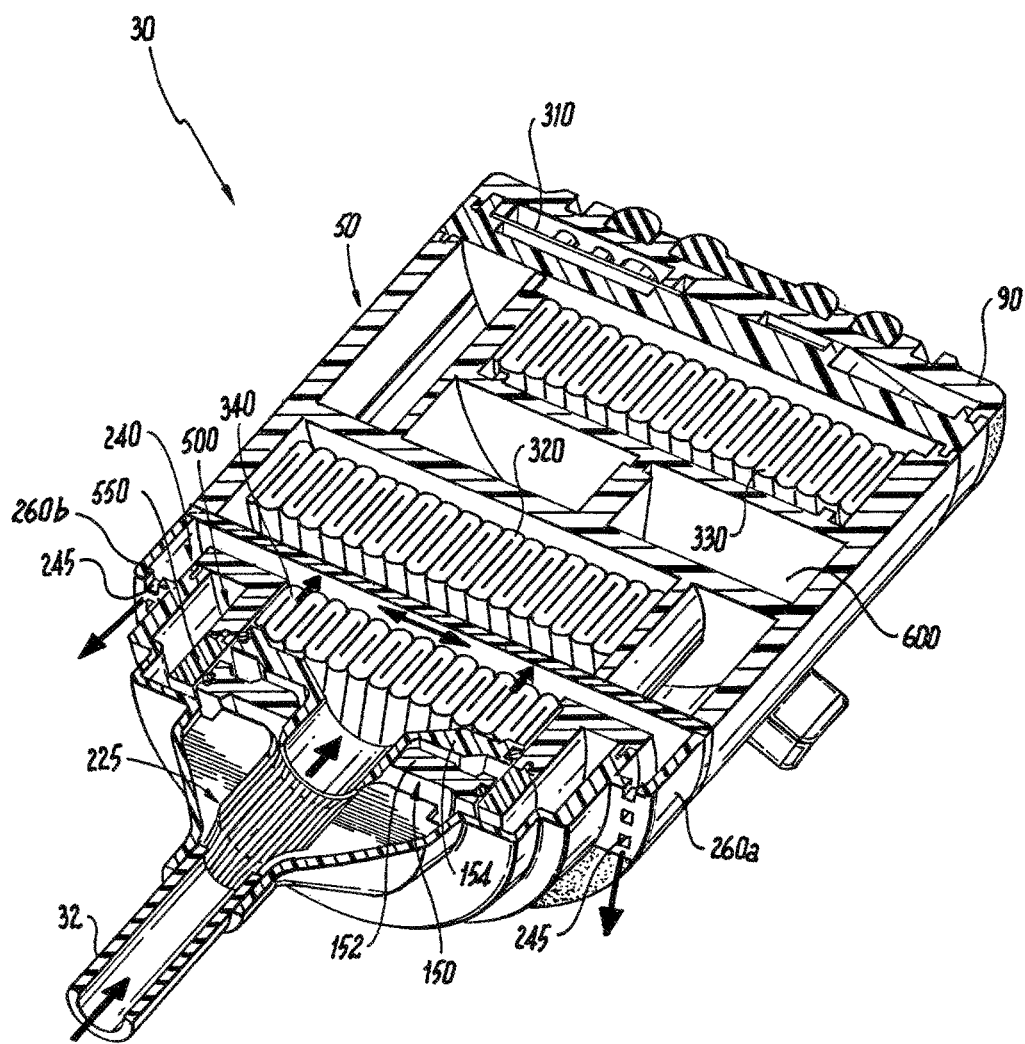
FIG. 9 is a cross-sectional view of the gas conditioning unit taken along line 9-9 of FIG. 3, with directional arrows illustrating the smoke evacuation flow path extending from the primary central port in the front end of the filter housing to the vents in the front end of the filter housing.

The gas conditioning unit 30 of the subject invention also includes a smoke evacuation flow path 240 indicated by the directional arrows shown in FIG. 9. Flow path 240 is configured to convey smoke and debris from the body cavity 15, which his generated during surgery by using tissue ablation devices, electro-cautery devices or the like. In normal operation, this flow could range from 3 to 8 liters per minute. As a result, the abdominal cavity, or lumen as the case may be, remains clear and visibility is maintained throughout the surgical procedure.

Figure 10:
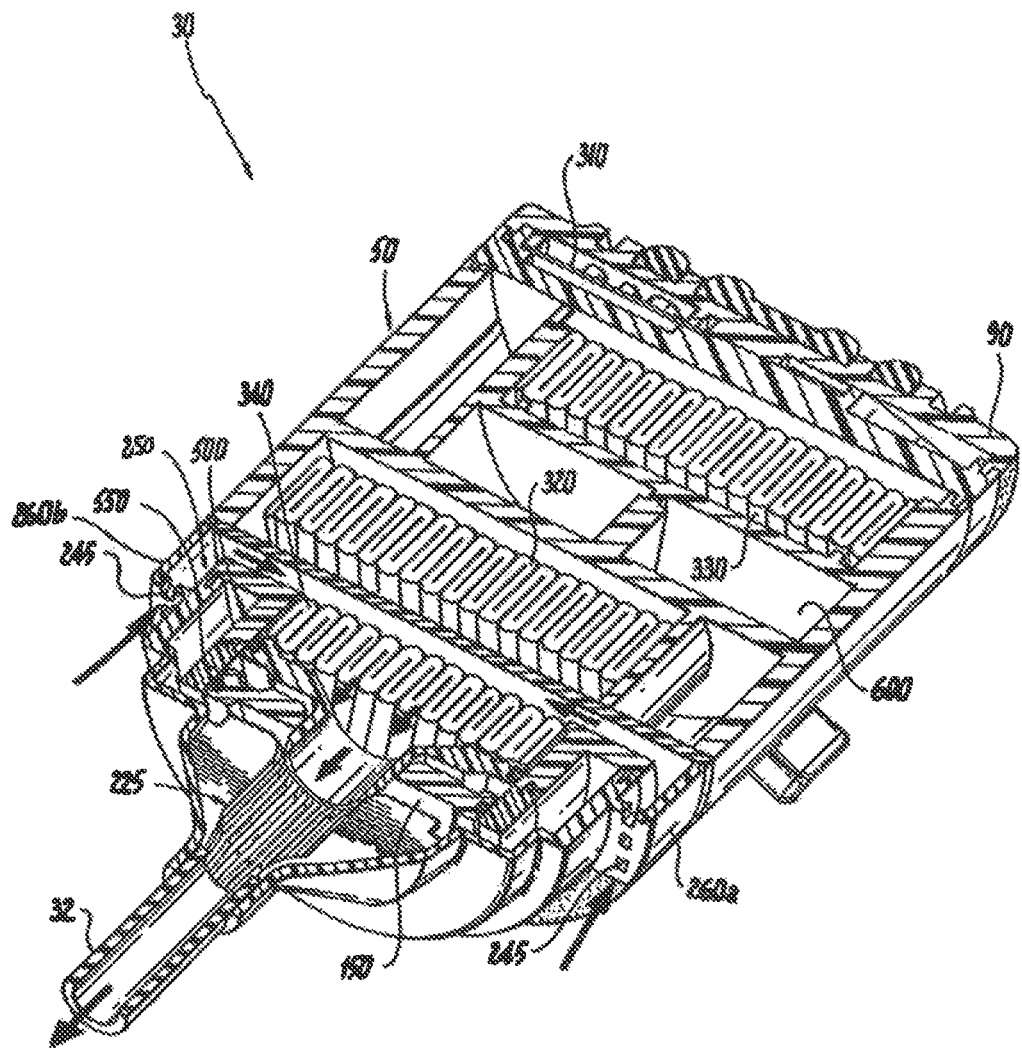
FIG. 10 is a cross-sectional view of the gas conditioning unit taken along line 10-10 of FIG. 3, with directional arrow illustrating the air entrainment flow path extending from the primary central port in the front end of the filter housing to the vents in the front end of the filter housing.

The gas conditioning unit 30 also includes an air entrainment flow path 250 indicated by the directional arrows shown in FIG. 10, which is configured to draw air into the body cavity or lumen to maintain a given pressure therein under certain abnormal operating conditions. For example, if a significant leak arises during a surgical procedure, air will be entrained into the body cavity to maintain the pneumoperitoneum. Air could also be entrained into the body cavity through flow path 250 during heavy suction events, when a significant volume of gas is purposefully removed from the abdominal cavity. This is a safety feature of the gas delivery system 10. This is not intended to occur under normal operating conditions.

Referring once again to FIG. 2, the gas conditioning unit 30 is adapted and configured for ready installation into and removal from the housing 14 of gas delivery device 12 by way of an interfitting lug arrangement. More particularly, the generally cylindrical housing 50 of gas conditioning unit 30 includes a plurality of circumferentially spaced apart engagement lugs, including an L-shaped lug 52 and a square-shaped lug 54. A third lug 56 can be seen in FIG. 12.

The three engagement lugs 52, 54 and 56 are dimensioned and configured to interact with correspondingly shaped and positioned recesses 62, 64 and 66 defined in the periphery of the cartridge engagement port 60 formed in the front panel of housing 14, as shown in FIG. 2.

Figure 3:
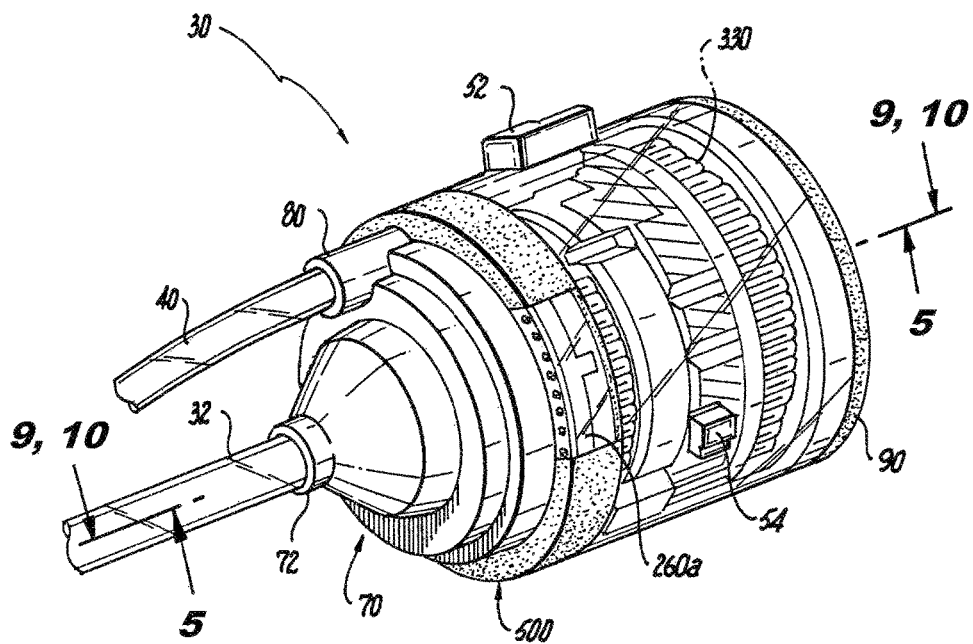
FIG. 3 is a perspective view of the gas conditioning unit of the subject invention as viewed from the front end of the unit, illustrating the two gas flow conduits extending therefrom.
Figure 4:
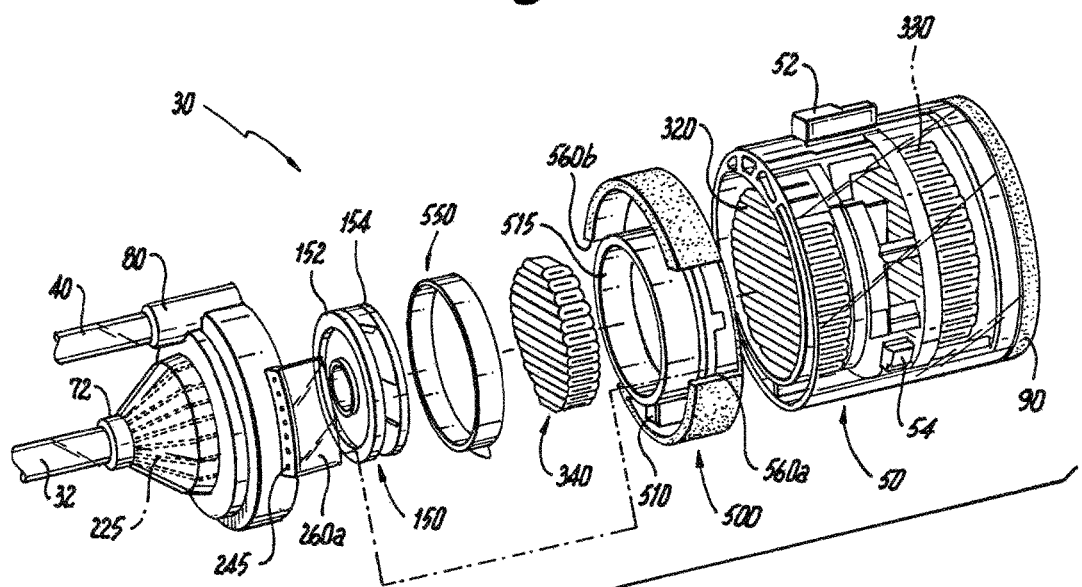
FIG. 4 is an exploded perspective view of the gas conditioning unit of the subject invention, with parts separated for ease of illustration.
Figure 5:
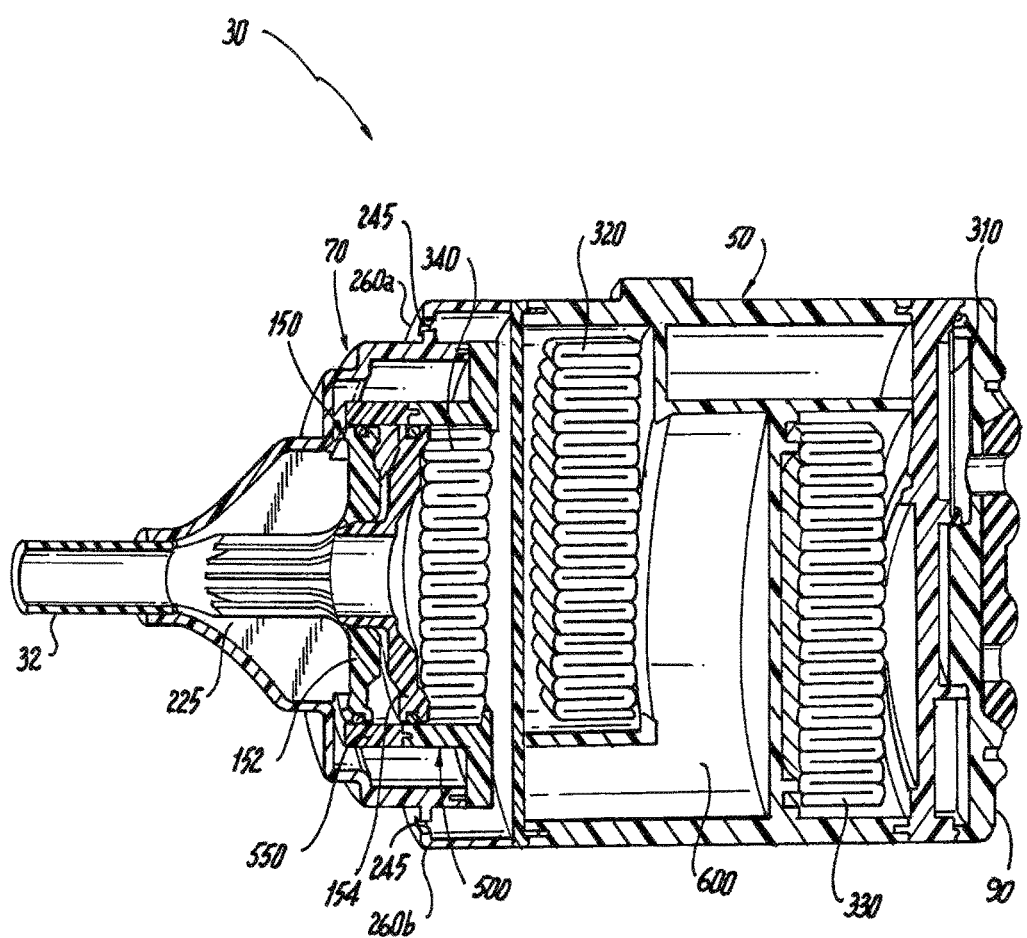
FIG. 5 is a cross-sectional view of the gas conditioning unit taken along line 5-5 of FIG. 3, illustrating the annular jet rings which form the internal nozzle assembly of the gas conditioning unit, the throat region in which the internal gaseous seal is formed and the four filters for conditioning gas flowing through the unit.

Referring to FIGS. 2 through 4, the housing 50 of gas conditioning unit 30 includes a front end cap or cover 70 and a rear end cap or cover 90. The front end cap 70 has two conduit connections associated therewith. There is a first or central conduit connection 72 that is operatively associated with the first conduit 32, shown in FIGS. 1 and 2. Front end cap 70 also includes a second conduit connection 80 operatively associated with the second conduit 40, which is also shown in FIGS. 1 and 2.

The rear end cap 90 includes three ports, each having an associated elastomeric sealing ring for proving a sealed interface with a seating area defined in the cartridge engagement port 60. The first port 92 is a gas inlet surrounded by a seal 93 and it communicates with the pressure path 220 shown in FIG. 7, and ultimately with tube 32.

The second port 94 is a gas inlet surrounded by a seal 95 and it communicates with the sense/insufflation path 210 shown in FIG. 6, and ultimately with tube 80. The third port 96 is a gas outlet surrounded by a seal 97 and it communicates with the vacuum return path 230 shown in FIG. 8. This path leads back to the pump 20 in delivery device 12.

Each flow path defined within the filter housing 50 has a filter element associated therewith for conditioning gas flowing therethrough. The vacuum return flow path 230 shown in FIG. 8 has a disc-shaped pleated filter element 330 associated therewith for filtering the spent or depressurized fluid going to the compressor pump 20 from the nozzle assembly 150. The pressurized gas flow path 220 shown in FIG. 7 has a disc-shaped pleated filter element 320 associated therewith for filtering pressurized gas coming from the compressor pump 20 to the nozzle assembly 150.

The sensing/insufflation gas flow path 210 shown in FIG. 6 has a non-woven membrane filter element 310 associated therewith. The smoke evacuation flow path 240 shown in FIG. 9 and the air entrainment flow path 250 shown in FIG. 10, share a common disc-shaped pleated filter element 340 for filtering smoke and other debris from the patient's abdominal cavity when operating in a smoke evacuation mode and for filtering entrained air drawn into the system 10 under certain operating conditions. The pleated filter elements can be formed from suitable materials such as for example LydAir MG Grade 6850 media or the like and can have a porosity and filtration efficiency that is sufficient to meet ULPA standards.

Referring to FIGS. 3 and 4, the front end cap 70 of the filter housing 50 includes a side outlet port 80 communicating with the insufflation/sensing gas flow path 210, and a primary central port 72 communicating with the smoke evacuation flow path 240 and the air entrainment flow path 250. The front end cap 70 of filter housing 50 further includes a plurality of apart vent ports 245 communicating with the smoke evacuation flow path 240 of FIG. 9 and the air entrainment flow path 250 of FIG. 10. Preferably, the vent ports 245 in the front end cap 70 of the filter housing 50 are provided on diametrically opposed flanges 260*a* and 260*b*, and they are all open to atmosphere.

The filter housing 50 preferably includes an internal pressure chamber formed within the pressurized gas flow path 220 that is located upstream from the internal nozzle assembly 150. The pressure chamber is formed by an inlet diverter plate 500 that is welded to the housing 50. The diverter plate 500 includes an infusion port 510 that receives pressurized gas from the pump 20 through flow path 220 downstream from filter element 320. The infusion port 510 communicates with the nozzle assembly 150 by way of a surrounding pressure ring 550. The inlet diverter plate 500 functions to divert the pressurized gas flow around the smoke evacuation flow path 240 and the air entrainment flow path 250. Furthermore, the inlet diverter plate 500 defines a cavity 515 for accommodating the pleated filter 340 that is associated with the smoke evacuation path 240 and the air entrainment path 250. In addition, the diverter plate includes opposed arcuate gaps 560a and 560b for accommodating the opposed arcuate flanges 260a and 260b provided on the front end cap 70.

The filter housing 50 of conditioning unit 30 further includes an internal reservoir chamber 600 located within the vacuum return flow path 230 shown in FIG. 8, upstream from the pump 20. The reservoir 600 is adapted and configured to retain any fluid or debris that makes its way past the filter element 340 in smoke evacuation path 240. The reservoir 600 includes a sensing assembly designed to monitor the level of fluid that accumulates within the filter housing 50, to maintain a safe operation of the system 10. The sensing assembly is more fully described in in commonly assigned U.S. Pat. No. 9,067,030, which is incorporated herein by reference in its entirety.

Referring to FIG. 11, there is illustrated to two trocars or cannulae that are employed with the gas delivery system 10 of the subject invention for laparoscopic surgical procedures in which insufflation/sensing, recirculation and smoke evacuation can be conducted as explained in detail hereinabove. These are the devices 34 and 42 which are also illustrated in FIG. 1. Trocar 34 is the primary access port for the system and it includes a standard mechanical seal, such as for example, a duckbill seal or the like (not shown). Trocar 34 is equipped with a large luer fitting 34a that is greater in diameter than a standard luer fitting, so that it can be readily connected to the central conduit 32 of gas conditioning unit 30. Trocar 42 is the secondary access port of the system and it also includes a standard mechanical seal, such as a duckbill seal or the like (not shown). Trocar 42 includes a standard sized luer fitting 42a that is adapted and configured to connect with the insufflation/sensing line 40 of gas conditioning unit 30.

Figure 12:
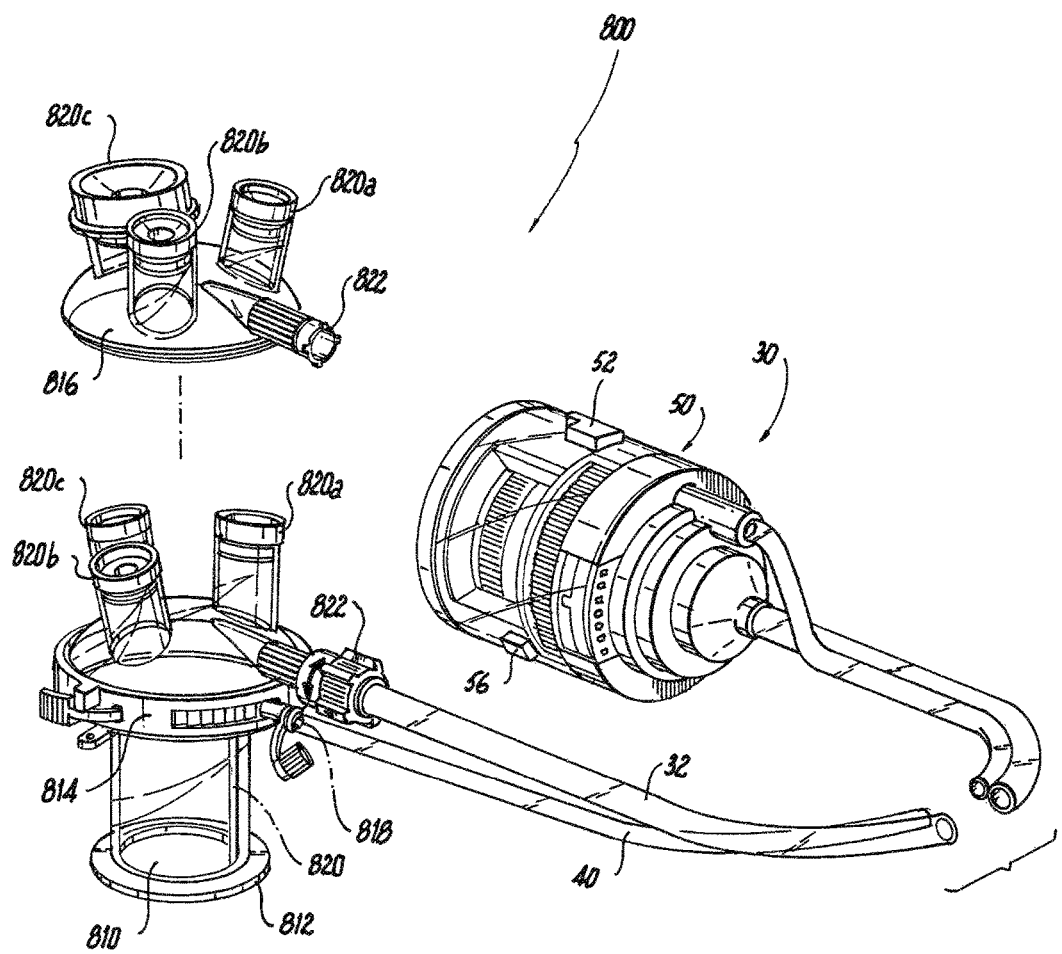
FIG. 12 is a perspective view of the gas conditioning unit of the subject invention, in conjunction with a multi-port access device configured for use in single incision laparoscopic surgical procedures and trans-anal minimally invasive surgical procedures.

Referring now to FIG. 12, there is illustrated a multi-port access device designated generally by reference numeral 800 that is configured for use in single incision laparoscopic procedures and trans-anal minimally invasive surgical procedures in conjunction with the gas conditioning unit 30 of the subject invention. The multi-port access device 800 includes an elongated tubular body portion 810 adapted and configured for introduction into through a natural orifice of a body lumen or through a single incision formed in the abdominal wall of a patient.

The body portion 810 includes a distal annular flange 812 for securing the body portion 810 against the inner surface of the abdominal wall in the case of a single incision laparoscopic procedure. An adjustable engagement ring 814 is operatively associated with the proximal end of the body portion 810 for receiving and retaining multiport end cap or cover 816. The engagement ring 814 includes a standard luer fitting 818 for connecting with the insufflation/sensing line 40 of the conditioning unit 30. The fitting 818 leads to a conduit tube 820 that runs along the interior wall of the body portion 810. The conduit tube 820 delivers insufflation gas into the body cavity or lumen and also serves as the pressure sensing conduit for access device 800.

The multiport end cap cover 816 includes a large (non-standard) luer fitting 822 for connecting with the main or central conduit 32 associated with the conditioning unit 30 of the subject invention. As explained previously, the central conduit 32 leads to the connector 72 of end cap 70 and it communicates with the pressure barrier formed within the throat region 225 of the end cap 70, and with the smoke evacuation path 240 and air entrainment path 250 of gas conditioning unit 30.

The multiport end cap or cover 816 is preferably removable from the tubular body portion 810 and it includes three separate access ports 820a-820c. The access ports 820a-820c of cover 816 can all be configured to receive endoscopic instruments have common diameter (i.e., 5 mm instruments) or the access ports 820a-820c of cover 816 could be configured to receive endoscopic instruments of different diameters (i.e., 12 mm and 5 mm instruments).

While the subject invention have been shown and described with reference to a preferred embodiment, those skilled in the art will readily appreciate that various changes and/or modifications may be made thereto without departing from the spirit and scope of the subject invention as defined by the appended claims.

What is claimed is:

1. A system for delivering gas during a surgical procedure performed within a patient's body cavity or through a patient's body lumen, comprising:
   a) a gas delivery device having a main housing including a port for receiving insufflation gas from a gas source and enclosing a pump assembly for circulating gas throughout the system; and
   b) a gas conditioning unit configured for operative association with the gas delivery device and defining:
      i) an insufflation gas flow path for delivering insufflation gas to the patient's body cavity or body lumen and for facilitating periodic static pressure measurements from the patient's body cavity or body lumen;
      ii) a pressurized gas flow path for delivering pressurized gas from the pump to an internal nozzle assembly configured to accelerate the pressurized gas to generate a continuous pressure barrier contained within the gas conditioning unit that inhibits egress of insufflation gas from the patient's body cavity or body lumen;
      iii) a vacuum return flow path for returning depressurized gas spent by the internal nozzle assembly back to the pump under vacuum;
      iv) an air entrainment flow path for drawing air into the patient's body cavity or body lumen to maintain a given pressure therein under certain abnormal operating conditions; and
      v) a smoke evacuation flow path for conveying smoke and debris from the patient's body cavity or body lumen, wherein the air entrainment flow path and the smoke evacuation flow path comprise a common bi-directional flow path that is open to atmosphere when the gas conditioning unit is installed in the gas delivery device and the insufflation gas flow path, the pressurized gas flow path and the vacuum return flow path are in fluid communication with the patient's body cavity or body lumen.

2. A system as recited in claim 1, wherein the gas conditioning unit includes a generally cylindrical filter housing having a front end and an opposed rear end, and wherein the main housing of the gas delivery unit includes an engagement port for detachably receiving the rear end of the gas conditioning unit.

3. A system as recited in claim 2, wherein each flow path is defined within the filter housing and has a filter element associated therewith for conditioning gas flowing therethrough.

4. A system as recited in claim 3, wherein the air entrainment flow path and the smoke evacuation flow path share a common filter element in the form of a pleated filter element.

5. A system as recited in claim 3, wherein the vacuum return flow path and the pressurized gas flow path each have a separate pleated filter element associated therewith.

6. A system as recited in claim 3, wherein the insufflation gas flow path has a non-woven membrane filter element associated therewith.

7. A system as recited in claim 2, wherein the rear end of the filter housing includes a first inlet port communicating with the insufflation gas flow path.

8. A system as recited in claim 7, wherein the first inlet port in the rear end of the filter housing communicates with the source of insufflation gas.

9. A system as recited in claim 2, wherein the rear end of the filter housing includes a second inlet port communicating with the pressurized gas flow path.

10. A system as recited in claim 9, wherein the second inlet port in the rear end of the filter housing communicates with an outlet of the pump.

11. A system as recited in claim 2, wherein the rear end of the filter housing includes a first outlet port communicating with the vacuum return path.

12. A system as recited in claim 11, wherein the first outlet port in the rear end of the filter housing communicates with an inlet of the pump.

13. A system as recited in claim 2, wherein the front end of the filter housing includes a second outlet port communicating with the insufflation gas flow path.

14. A system as recited in claim 13, wherein a first surgical access device is in fluid communication with the second outlet port of the filter housing through a first flexible tube.

15. A system as recited in claim 2, wherein the front end of the filter housing includes a primary central port communicating with the smoke evacuation flow path and the air entrainment flow path.

16. A system as recited in claim 15, wherein a second surgical access device is in fluid communication with the primary central port of the filter housing through a second flexible tube.

17. A system as recited in claim 2, wherein the front end of the filter housing includes a plurality of spaced apart vent ports communicating with the smoke evacuation flow path and the air entrainment flow path.

18. A system as recited in claim 17, wherein the plurality of vent ports in the filter housing are open to atmosphere.

19. A system as recited in claim 2, wherein the filter housing includes an internal pressure chamber within the pressurized gas flow path located upstream from the internal nozzle assembly.

20. A system as recited in claim 2, wherein the filter housing includes an internal reservoir chamber located within the vacuum return flow path upstream from the pump.

21. A gas conditioning unit for use with a surgical gas delivery device, the gas conditioning unit comprising:
a filter housing having an insufflation gas flow path for delivering insufflation gas to a body cavity or body lumen and for facilitating periodic static pressure measurements from the body cavity or body lumen,
a pressurized gas flow path for delivering pressurized gas from a pump in the surgical gas delivery device to an internal nozzle assembly in the filter housing that accelerates the pressurized gas and thereby generates a continuous gaseous pressure barrier that inhibits egress of insufflation gas from the body cavity or body lumen,
a vacuum return flow path for returning depressurized gas spent by the internal nozzle assembly back to the pump under vacuum, an air entrainment flow path for drawing air into the body cavity or body lumen to maintain a given pressure therein, and
a smoke evacuation flow path for conveying smoke from the body cavity or body lumen, wherein the air entrainment flow path and the smoke evacuation flow path comprise a common bi-directional flow path that is open to atmosphere when the gas conditioning unit is installed in the surgical gas delivery device and the insufflation gas flow path, the pressurized gas flow path and the vacuum return flow path are in fluid communication with the body cavity or body lumen.

22. A gas conditioning unit as recited in claim 21, wherein each flow path is defined within the filter housing and has a filter element associated therewith for conditioning gas flowing therethrough.

23. A gas conditioning unit as recited in claim 22, wherein the air entrainment flow path and the smoke evacuation flow path share a common disc-shaped filter element in the form of a pleated filter element.

24. A gas conditioning unit as recited in claim 22, wherein the vacuum return flow path and the pressurized gas flow path each have a separate disc-shaped pleated filter element associated therewith.

25. A gas conditioning unit as recited in claim 22, wherein the insufflation gas flow path has a non-woven membrane filter element associated therewith.

26. A gas conditioning unit as recited in claim 21, wherein a rear end of the filter housing includes a first inlet port communicating with the insufflation gas flow path, a second inlet port communicating with the pressurized gas flow path, and a first outlet port communicating with the vacuum return path.

27. A gas conditioning unit as recited in claim 26, wherein the first inlet port in the rear end of the filter housing communicates with a source of insufflation gas.

28. A gas conditioning unit as recited in claim 26, wherein the second inlet port in the rear end of the filter housing communicates with an outlet of the pump, and the first outlet port in the rear end of the filter housing communicates with an inlet of the pump.

29. A gas conditioning unit as recited in claim 21, wherein a front end of the filter housing includes a second outlet port communicating with the insufflation gas flow path, a primary central port communicating with the smoke evacuation flow path and the air entrainment flow path, and a plurality of spaced apart vent ports communicating with the smoke evacuation flow path and the air entrainment flow path.

30. A gas conditioning unit as recited in claim 29, wherein the plurality of vent ports in the filter housing are open to atmosphere.

31. A gas conditioning unit as recited in claim 21, wherein the filter housing includes an internal pressure chamber within the pressurized gas flow path located upstream from the internal nozzle assembly.

32. A gas conditioning unit as recited in claim 21, wherein the filter housing includes an internal reservoir chamber located within the vacuum return flow path upstream from the pump.

* * * * *